United States Patent [19]

Heiskel et al.

[11] Patent Number: 5,620,631
[45] Date of Patent: Apr. 15, 1997

[54] PRESSURIZED-GAS PACK AND PROPELLANT FOR AEROSOLS

[75] Inventors: Elmar Heiskel, Dreieich; Wilfred Schmieder, Hofheim am Taunus, both of Germany

[73] Assignee: Solvay (Sociéte Ananyme), Brussels, Belgium

[21] Appl. No.: 465,521

[22] Filed: Jun. 5, 1995

Related U.S. Application Data

[63] Continuation of Ser. No. 88,627, Jul. 6, 1993, which is a continuation of Ser. No. 483,118, Feb. 22, 1990, abandoned.

[30] Foreign Application Priority Data

Feb. 24, 1989 [DE] Germany ........................... 39 05 726.7

[51] Int. Cl.$^6$ .............................. C11D 17/00; A61L 9/12; C09K 3/30
[52] U.S. Cl. .............................. 252/305; 424/45; 510/140
[58] Field of Search .................................. 252/305, 364, 252/90; 424/45, 47; 510/140, 406, 412

[56] References Cited

U.S. PATENT DOCUMENTS

| | | | |
|---|---|---|---|
| 2,968,628 | 1/1961 | Reed | 252/305 |
| 2,981,763 | 4/1961 | Neill et al. | 260/653.8 |
| 3,047,640 | 7/1962 | Sweeney et al. | 260/653.4 |
| 3,354,088 | 11/1967 | Elmquist | 252/90 X |
| 3,583,921 | 6/1971 | Healy et al. | 252/90 |
| 4,158,023 | 6/1979 | Von Halasz | 570/166 |
| 4,174,295 | 11/1979 | Bargigia et al. | 252/305 |
| 4,655,959 | 4/1987 | Stopper | 252/305 |
| 5,002,757 | 3/1991 | Gulpta | 252/305 X |
| 5,073,206 | 12/1991 | Wilson et al. | 252/305 X |
| 5,118,494 | 6/1992 | Schultz et al. | 424/45 |
| 5,474,759 | 12/1995 | Fassberg et al. | 424/45 |

FOREIGN PATENT DOCUMENTS

| | | |
|---|---|---|
| 1542076 | 3/1970 | Germany. |
| 902590 | 8/1962 | United Kingdom. |
| 1298263 | 11/1972 | United Kingdom. |
| 2125426 | 3/1984 | United Kingdom. |

OTHER PUBLICATIONS

Hawley's Condensed Chemical Dictionary, Van Nostrand Reinhold Co, Inc., NY, NY (1987) pp. 302–303.

Fessenden & Fessenden, Organic Chemistry, Willard Grant Press, Boston, Mass (1979) pp. 20–21.

Journal of Physical Chemistry, 66, 635–639 (1962) "Second Virial Coefficients for the system: n–Butane +Perfluoro–n–butane and dimethyl ether+1–hydroperfluoropropane".

Translation of DE 1 542 076 (Date of translation unknown).

Paul A. Sanders, Principles of Aerosol Technology, (Van Nostand Reinhold Company, NY, NY, 1974) pp. 192.

Morrison and Boyd, Organic Chemistry, Fourth Edition, (Allyn & Bacon, Inc., Boston, MA, 1983), pp. 198–200.

CRC Handbook of Chemistry and Physics, 63rd Edition, 1982–1983 (CRC Press, 1982).

Derwent File Supplier Japs, Abstract of JP 62 093 211, "Aerosol Composition" (1987).

Primary Examiner—Richard D. Lovering
Assistant Examiner—Daniel S. Metzmaier
Attorney, Agent, or Firm—Connolly & Hutz

[57] ABSTRACT

The invention relates to a pressurized-gas pack, in particular an aerosol pressurized-gas pack, containing pressure-liquefied 2-hydro-heptafluoropropane (F 227) or a mixture thereof with pressure-liquefied propane and/or n-butane and/or i-butane and/or dimethyl ether and/or 1,1-difluoroethane. The invention also relates to a propellant for aerosols, comprising F 227 or the named mixtures thereof.

4 Claims, No Drawings

PRESSURIZED-GAS PACK AND PROPELLANT FOR AEROSOLS

This application is a continuation of application Ser. No. 08/088,627 filed Jul. 6, 1993, pending, which is a continuation of Ser. No. 07/483,118 filed Feb. 22, 1990, now abandoned.

DESCRIPTION

For decades aerosol pressurized-gas packs, abbreviated to aerosols, have been produced using pressure-liquefied gases (in some cases also compressed gases) as the propellant and used for various purposes. The pressure-liquefied gases (also referred to as "liquid gases" in the text which follows) which are used are, in the main, the inflammable gases propane/butane (P/B) and dimethyl ether (DME), and the non-inflammable fluorochlorohydrocarbons (FCHC), principally the types 12 (dichlorodifluoromethane) and 114 (dichlorotetrafluoroethane).

A certain safety hazard is associated with the inflammable liquid gases. For this reason the non-inflammable and toxicologically acceptable FCHC have been used preferentially in the past. The compressed gases such as $CO_2$ or $N_2$, which are also non-inflammable, can be used only in special cases, because they are unable to maintain a constant pressure which is independent of the degree of evacuation in the pressurized-gas pack.

Since the publication of the ozone theory (degradation of ozone by FCHC and other chlorine-containing organic compounds) liquid gases have been sought which are suitable as propellant and are neither inflammable nor able to degrade ozone and which also are not injurious to health.

Pressurized-gas packs which are very different in respect of their application properties can be produced using pressure-liquefied gases. Pressurized-gas packs always comprise a pressure container, preferably of metal or glass, fitted with a valve construction for withdrawing the contents from the pack, and the filling material present in the container. The filling material can be of very diverse nature.

In the simplest case it comprises only a single pressure-liquefied gas, which, on operating the valve, is released from containers not fitted with a riser tube, from the gas phase, i.e. in the gaseous state, into the open air, creating a (puff) effect similar to compressed air. Such products are used for the removal of dust from, for example, glass surfaces, such as camera lenses.

However, in by far the majority of cases the contents of the container comprise a so-called filling product (often also called an active compound solution), which is intended to be sprayed, and a propellant in the form of a pressure-liquefied gas or gas mixture, which in the liquid phase is miscible with the liquid filling product in all proportions, i.e. forms only a single liquid phase, above which a gas phase forms. Examples of such "true" aerosol products, which are sprayed from the pack as a mist, are, for example, insecticide spray, room spray and deodorant spray. They have relatively high propellant contents (greater than 50%). Their ability to function is conditional upon complete miscibility of the solvent used in the filling product with the liquefied propellant gas (mixture) and the use of a valve with a riser tube that reaches to the bottom of the container.

Another type of aerosol products are the foam aerosols, in which, because of a lack of miscibility, the liquid components of the filling product (for example water) do not form a homogeneous liquid phase with the pressure-liquefied propellant gas, but form two separate liquid phases. By shaking the container an emulsion (normally an O/W, i.e. "oil-in-water", emulsion) forms from the two liquid phases in the presence of a surfactant. On leaving the container through a valve with a "foam head" the emulsion is converted, as a result of the abrupt evaporation of the oil phase (i.e. the liquid gas droplets), into a foam which has a volume 200 to 300 times greater than that of the emulsion. Such foam aerosols are principally used in the cosmetics sector (for example, shampoo, shower foam, sun-screen foam). A pre-requisite for their preparation is that the filling product and the liquid gas do not mix homogeneously, which signifies a very low solubility of the liquid gas phase in the liquid filling-product phase; this is generally the case if the filling product is aqueous, i.e. "water-based".

Propellant mixtures have already been disclosed in DE-OS 1,542,076 which contain a relatively water-soluble propellant from the group of liquefied halogenated hydrocarbons and a relatively water-insoluble propellant from the same group. In this specification 2H-heptafluoropropane is named as an example of a relatively water-insoluble propellant.

The present invention relates to a propellant for aerosols, comprising pressure-liquefied 2-hydro-heptafluoropropane (F227) or a mixture thereof with pressure-liquefied propane and/or n-butane and/or i-butane and/or dimethyl ether and/or 1,1-difluoroethane. The propellant is preferably a mixture of F227 with propane and/or n-butane and/or i-butane and/or dimethyl ether.

F227 can, however, also be used for blowing dust from, for example, glass surfaces such as camera lenses. In this case an appropriate pressurized-gas pack contains only pressure-liquefied F227.

In contrast to this an aerosol pressurized-gas pack contains a filling product in addition to F227 or the named mixtures thereof (as propellant), and the propellant and the filling product can form either a single liquid phase or two liquid phases.

Aerosol pressurized-gas packs in which the filling product contains water as the liquid component are a particularly important case; here the filling product is generally an aqueous solution, but sometimes also a suspension. In this case a second liquid (namely aqueous) phase is always present in addition to the pressure-liquefied propellant (F227 or the named mixtures thereof).

The pressure-liquefied mixture components propane, n-butane, i-butane, dimethyl ether and 1,1-difluoroethane all have a density of less than 1 $g/cm^3$, whilst F227 has a density of more than 1 $g/cm^3$. Therefore mixtures having a density of approximately 1 $g/cm^3$ can be prepared from F227 and the named mixture components. Such mixtures therefore have a density which is the same as or very similar to that of an aqueous phase and are therefore very suitable as propellants for water-based aerosols. In appropriate pressurized-gas packs stable O/W emulsions already form on the first shaking and these do not separate again into two continuous phases even after prolonged standing and therefore do not need to be shaken again before further use. The following are particularly suitable propellant mixtures for water-based aerosols:

1. A mixture of F 227 and propane/n-butane (ratio by mass 15:85) in the ratio by mass of 65:35 to 85:15, preferably 70:30 to 80:20, and in particular about 75:25.
2. A mixture of F 227 and i-butane in the ratio by mass of 65:35 to 85:15, preferably 70:30 to 80:20, and in particular about 74:26.

3. A mixture of F 227 and propane/i-butane (ratio by mass 65:35) in the ratio by mass of 70:30 to 90:10, preferably 75:25 to 85:15, and in particular about 80:20.
4. A mixture of F 227 and 1,1-difluoroethane (F 152 a) in the ratio by mass of 35:65 to 45:55, and in particular about 40:60.

Preferably one of the propellant mixtures 1 to 3 is used.

EXAMPLES

The following liquid gas/propellant mixtures I to V were prepared:

|  | I (% by mass) | II (% by mass) | III (% by mass) | IV (% by mass) | V (% by mass) |
| --- | --- | --- | --- | --- | --- |
| Components |  |  |  |  |  |
| F 227 | 76.0 | 65.0 | 40.0 | 74.0 | 80.0 |
| Propane | 3.6 | — | — | — | 13.0 |
| n-Butane | 20.4 | — | — | — | — |
| i-Butane | — | — | — | 26.0 | 7.0 |
| F 152 a | — | — | 60.0 | — | — |
| DME | — | 35.0 | — | — | — |
| Total | 100.0 | 100.0 | 100.0 | 100.0 | 100.0 |
| Density (kg/l) |  |  |  |  |  |
| 20° C. | 1.0 | 1.0 | 1.06 | 1.0 | 1.05 |
| 50° C. | 0.9 | 0.9 | 0.97 | 0.9 | 0.96 |
| Pressure (bar) |  |  |  |  |  |
| 20° C. | 3.6 | 4.7 | 5.3 | 3.5 | 5.3 |
| 50° C. | 8.2 | 10.7 | 11.4 | 8.0 | 11.5 |

Example 1 (shaving foams)

The following aerosol fillings were prepared in aerosol glass flasks fitted with commercially available aerosol valve and foam head:

| Filling product: | | |
| --- | --- | --- |
| 9.0 | % by mass | stearic acid |
| 1.0 | % by mass | polyglycol 400 |
| 1.0 | % by mass | polyglycol 1500 |
| 2.0 | % by mass | lauric acid monoethanolamide |
| 3.0 | % by mass | glycerol |
| 4.0 | % by mass | triethanolamine, technical grade |
| 80.0 | % by mass | distilled water |

The flasks were filled with the filling product in the ratio of
90% by mass filling product
10% by mass propellant mixture
with the propellant mixtures I, III, IV and V. In all 4 cases an emulsion which was stable on storage and which did not separate again into two continuous liquid phases even after standing for several months formed after shaking. On depressing the foam head, a fine-pored, stable foam formed in each case, the properties of which satisfied all demands to be made of a shaving cream. None of the foams, including those containing the propellant mixtures I, IV and V, could be ignited, in contrast to commercial available shaving foam aerosols which were filled into the containers using propane/butane.

Example 2 (shower foams)

As in Example 1, test fillings of aerosol shower foams were prepared to the following recipe:

| Filling product: | | |
| --- | --- | --- |
| 3.0 | % by mass | isopropyl myristate |
| 2.0 | % by mass | 1,2-propylene glycol |
| 60.0 | % by mass | Na alkylpolyglycol ether sulfate |
| 10.0 | % by mass | sarcoside of palm oil fatty acid |
| 25.0 | % by mass | distilled water |

Filling ratio:
90% by mass filling product
10% by mass propellant mixture
As in Example 1, the mixtures I, III, IV and V were used as propellant phase.
The results obtained were analogous to those in Example 1. These foams also proved to be non-inflammable.

Example 3 (body deodorant spray)

The following test fillings were prepared in aerosol glass flasks:

| Filling product: | | |
| --- | --- | --- |
| 96.1 | % by mass | ethanol (99.8%) |
| 0.5 | % by mass | 5-chloro-2-(2,4-dichlorophenoxy)-phenol |
| 1.0 | % by mass | isopropyl myristate |
| 0.4 | % by mass | perfume oil |
| 2.0 | % by mass | 1,2-propylene glycol |
| 100.0 | % by mass | |

Filling ratio:
30.0% by mass filling product
70.0% by mass propellant
In one case pure F 227 and in another case propellant mixture II was used as propellant. Both fillings possess very good spray characteristics and were stable on storage at −5° C. and at +40° C. In terms of odor, the filling containing the mixture II was also superior to the completely satisfactory filling containing pure 2-hydro-heptafluoropropane. According to EC law, the filling containing pure F 227 as propellant does not have to be labeled "INFLAMMABLE".

Example 4 (perfume spray)

A perfume spray was prepared using the following recipe:

| Filling product: | | |
| --- | --- | --- |
| 5.0 | % by mass | perfume oil |
| 95.0 | % by mass | ethanol (96%) |
| 100.0 | % by mass | |

Aerosol filling:
40.0% by mass filling product
60.0% by mass propellant=F 227
The test sample exhibited excellent spray characteristics and storage stability. No impairment of the scent by the propellant was detected. According to EC guidelines products prepared in accordance with this recipe do not have to be labeled "INFLAMMABLE".

We claim:

1. A pressurized-gas pack consisting essentially of 10% by mass of a propellant and 90% by mass of an aqueous filling product, the propellant consisting essentially of a mixture of a pressure-liquified 2-hydro-heptafluoropropane and propane and/or n-butane, and said 2-hydro-heptafluoropropane and propane and/or n-butane is in a ratio by mass of about 70:30 to 80:20, the ratio of the components of propellant-mixture being selected such that the mixture has approximately the same density as the aqueous filling product and said density being approximately 1 gram/cm$^3$ and the filling product consists essentially of stearic acid, polyglycol, lauric acid monoethanolamide, glycerol, triethanolamine and distilled water.

2. A pressurized-gas pack consisting essentially of 10% by mass of a propellant and 90 % by mass of an aqueous filling product, the propellant consisting essentially of a mixture of a pressure-liquified 2-hydro-heptafluoropropane and propane and/or n-butane wherein said 2-hydro-heptafluoropropane and propane and/or n-butane is in a ratio by mass of about 70:30 to 80:20, the ratio of the components of propellant-mixture being selected such that the mixture has approximately the same density as the aqueous filling product and said density being approximately 1 gram/cm$^3$ and wherein said filling product consists essentially of isopropyl myristate, 1,2-propylene glycol, Na alkylpolyglycol ether sulfate, sarcoside of palm oil fatty acid and distilled water.

3. A pressurized-gas pack consisting essentially of 10% by mass of a propellant and 90% by mass of an aqueous filling product, the propellant consisting essentially of a mixture of a pressure-liquified 2-hydro-heptafluoropropane and propane and/or n-butane wherein said 2-hydro-heptafluoropropane and propane and/or n-butane is in a ratio by mass of about 70:30 to 80:20, the ratio of the components of propellant-mixture being selected such that the mixture has approximately the same density as the aqueous filling product and said density being approximately 1 gram/cm$^3$, and wherein the filling product consists of 9% by mass of stearic acid, 1% by mass polyglycol 400, 1% by mass polyglycol 1500, 2% by mass lauric acid monoethanolamide, 3% by mass glycerol, 4% by mass triethanolamine and 80% by mass distilled water.

4. The pressurized-gas pack as claimed in claim 2, wherein said filling product consists essentially of 3% by mass isopropyl myristate, 2% by mass 1,2-propylene glycol, 60% by mass Na alkylpolyglycol ether sulfate, 10% by mass sarcoside of palm oil fatty acid and 25% by mass distilled water.

* * * * *